United States Patent [19]

Russell et al.

[11] Patent Number: 5,549,610

[45] Date of Patent: Aug. 27, 1996

[54] FEMORAL INTRAMEDULLARY NAIL

[75] Inventors: Thomas A. Russell, Memphis; John R. Pepper, Germantown, both of Tenn.

[73] Assignee: Smith & Nephew Richards Inc., Memphis, Tenn.

[21] Appl. No.: 332,343

[22] Filed: Oct. 31, 1994

[51] Int. Cl.⁶ .................................................. A61B 17/72
[52] U.S. Cl. .............................................. 606/64; 606/62
[58] Field of Search ................................ 606/62, 63, 64, 606/65, 66, 67, 68

[56] References Cited

U.S. PATENT DOCUMENTS 4,622,959  11/1986  Marcus ........................................ 606/64
4,976,258  12/1990  Richter et al. .............................. 606/64
5,122,141   6/1992  Simpson et al. ........................... 606/64
5,167,663  12/1992  Brumfield .................................. 606/64

*Primary Examiner*—Stephen C. Pellegrino
*Assistant Examiner*—Scott B. Markow
*Attorney, Agent, or Firm*—Pravel, Hewitt, Kimball, & Krieger

[57] ABSTRACT

An intramedullary femoral rod provides a hollow rod body with five openings including a first group of three openings and a second group of two openings spaced at 180° from the first opening. The five openings define three passageways including two upwardly oblique passageways for femoral repairs or one downwardly oblique passageway for recon repairs.

8 Claims, 3 Drawing Sheets

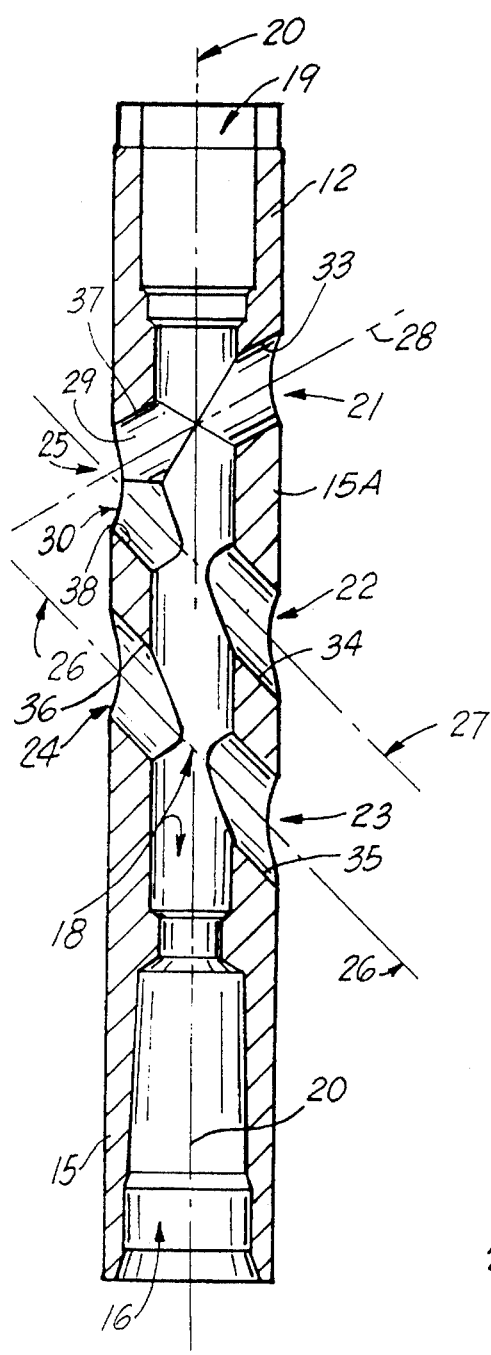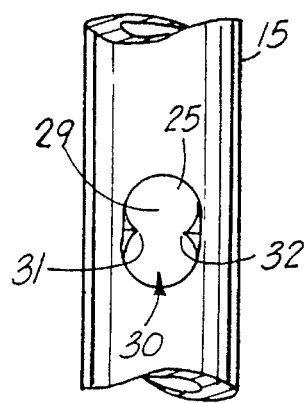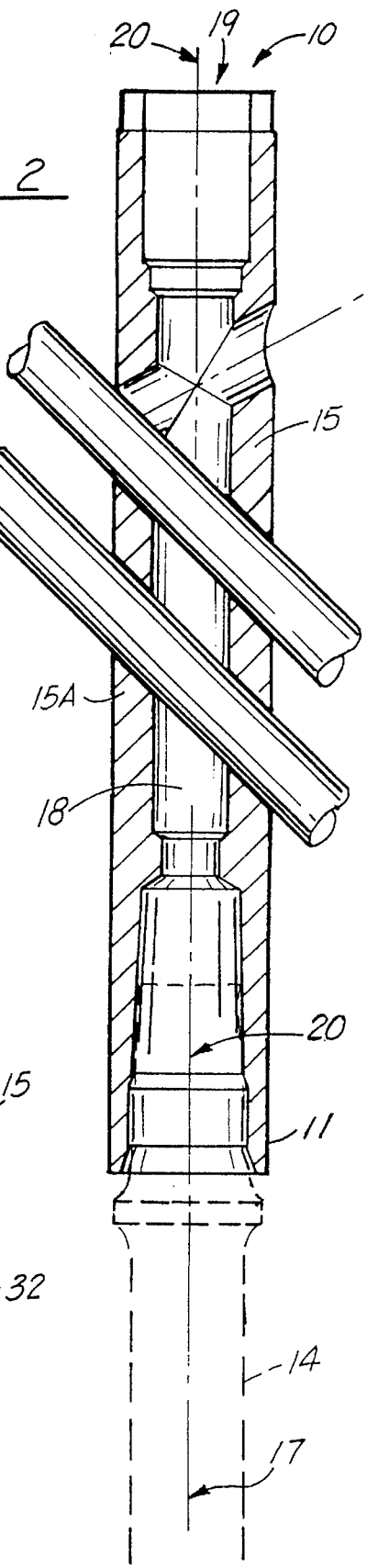

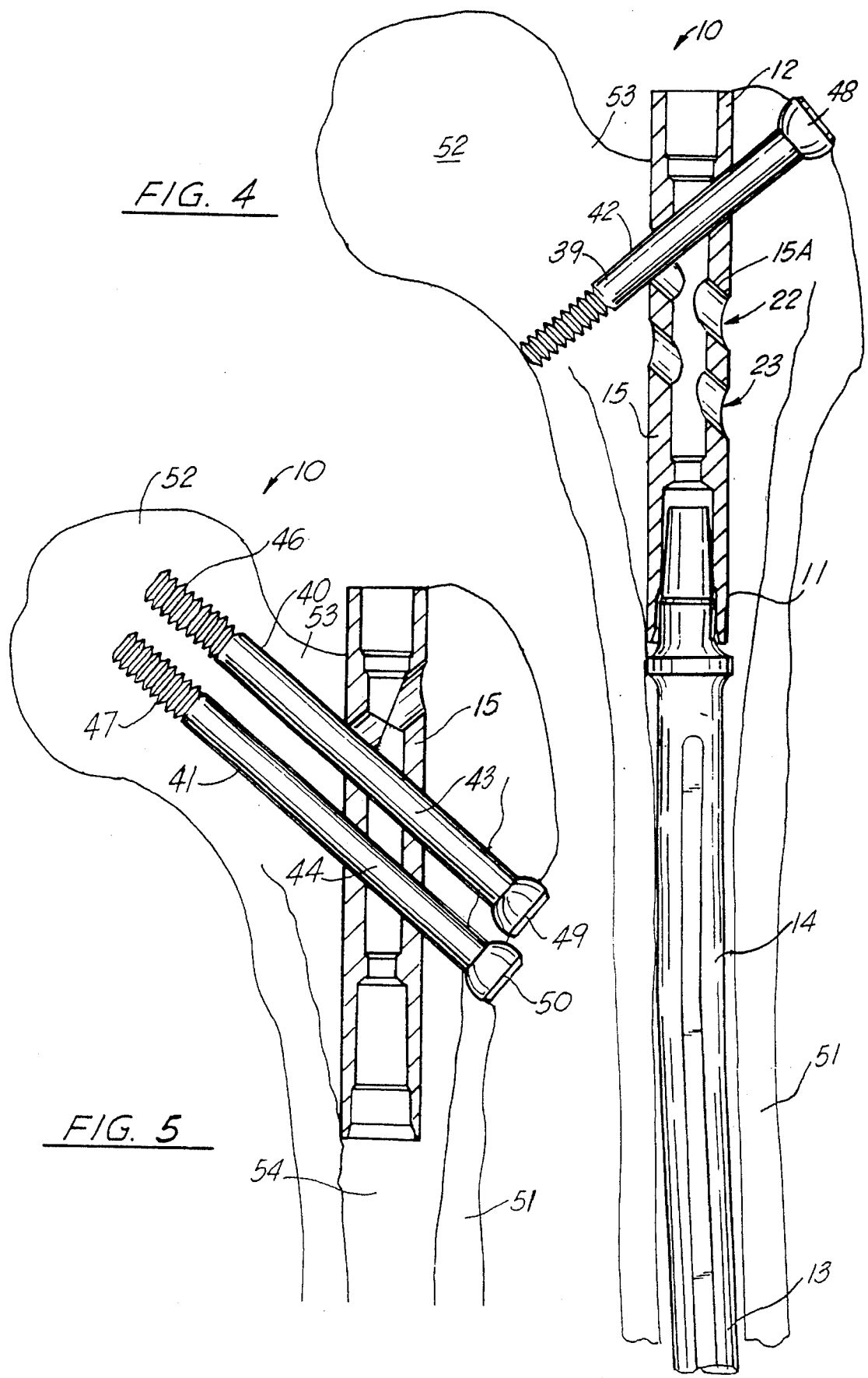

FEMORAL INTRAMEDULLARY NAIL

BACKGROUND OF THE INVENTION

1. Field of the Invention

The invention relates generally to devices for treating femoral fractures and, more particularly, to intramedullary rods and nails.

2. General Background

There are a variety of devices used to treat femoral fractures. Subtrochanteric and femoral shaft fractures have been treated with the help of intramedullary nails which are inserted into the marrow canal of the femur to immobilize the femur parts involved in fractures. An angled cross-nail or locking screw is inserted through the femur and the proximal end of the intramedullary rod. In some varieties, one or two screws may also be inserted through the femoral shaft and through the distal end of the intramedullary nail. The standard intramedullary nails have been successfully employed in treating fractures in lower portion of the femoral shaft.

Fractures of the neck, head or trochanters of the femur have been successfully treated with a variety of compression screw assemblies which include generally a compression plate having a barrel member, a lag screw and a compressing screw. The compression plate is secured to the exterior of the femur and the barrel member is inserted into a predrilled hole in the direction of the femoral head. The lag screw which has a threaded end and a smooth portion is inserted through the barrel member so that it extends across the break and into the femoral head. The threaded portion engages the femoral head. The compressing screw connects the lag screw to the plate. By adjusting the tension of the compressing screw the compression (reduction) of the fracture can be adjusted. The smooth portion of the lag screw must be free to slide through the barrel member to permit the adjustment of the compression screw. A number of patents to Brumfield, and the assignee of this application relate to intramedullary nail prothesis with transverse and diagonally extending bone screws including U.S. Pat. Nos. 4,827,917, 5,167,663, and 5,312,406.

The Russell-Taylor interlocking nail system manufactured by Smith and Nephew Richards, Inc. of Memphis, Tenn. includes an intramedullary rod having two pairs of holes through its proximal end. The axes of the pairs of holes intersect to provide a left or right orientation for insertion of a single locking screw. The screw is designed to pass from the greater to the lesser trochanter. There is not sufficient mechanical support to allow usage of the locking screw in the direction towards the femoral head because the second pair of holes weaken the nail when loaded in that direction. Further, the locking screw is a fully threaded screw which does not permit sliding of the screw relative to the intramedullary rod.

Compression screw assemblies are shown by the following patents: Fixel U.S. Pat. No. 4,432,358; Callender, Jr. U.S. Pat. No. 3,374,786; Pugh et al. U.S. Pat. No. 2,702,543; Griggs U.S. Pat. No. 4,530,355; Blosser, U.S. Pat. No. 3,094,120; and Wagner U.S. Pat. No. 3,842,825. The Blosser and Wagner patents illustrate the use of multiple screws to prevent rotation of the lag screw relative to the compression plate and barrel member. A surgical bone pin which functions like a lag screw and compressing screw but which does not include a compression plate is known by Cochran et al. U.S. Pat. No. 3,103,926.

A British patent GB 2,167,775A discloses an intramedullary nail for setting broken long bones. The nail has a head, a shank and a tip portion provided with an open ended groove for engaging a bolt previously inserted into the bone transverse to the bone axis to secure the nail to the bone. The Mareno patent 4,733,654 discloses an intramedullary nailing assembly that is adapted to the internal fixation of comminuted femoral fractures, which combines a conventional femoral nail, and extension and a set of pins interlocked with the nail and its extension. The extension is designed to be inserted into the proximal end of the femoral nail, and is predrilled to accept pins, some of which extend obliquely onto the femoral neck. A drill guide which can be inserted in the proximal end of the extension provides a convenient tool for predrilling the femur at the proper places and at the proper angles. The nail itself can be predrilled to receive pins on a bench mounted drilling guide.

The Chapman patent discloses a modular femoral fixation system for use in the treatment of femoral disorders resulting from injury, disease, or congenital defects. The apparatus includes at least three interconnectable components:

1) an elongated epiphyseal/metaphyseal implant,
2) intramedullary rod, and
3) an angled side plate having an elongated plate portion adapted to be secured to the outer cortical wall and a hollow sleeve adapted to extend into the femur. The epiphyseal/metaphyseal implant can be connected to either the angle side plate or the intramedullary rod. The system may also include an elongated bone plate connectable to the angle side plate, one or more additional epiphyseal/metaphyseal implants of variable length, and additional angled side plate, a distal buttress plate connectable to the elongated bone plates, and a plurality of bone screws of a universal design. Preferably, many or all of these components of the system are made of an inner, resilient titanium base alloyed.

The Grosse-Kempf nail manufactured by Howmedica Company of Rutherford, N.J. is believed to be one of the earliest intramedullary nailing devices introduced into the United States. The Grosse-Kempf nail includes a threaded hole in the intramedullary rod for receiving the interlocking screw. The fully threaded cannot slide through the threaded hole to permit the type of compression found in the compression screw assemblies discussed above. Furthermore, the axis of the threaded hole coincides with a line between the greater to lesser trochanter and not in the direction of the femoral neck.

Zickel U.S. Pat. No. 3,433,220, which issued on Mar. 18, 1969, discloses an intramedullary rod and cross-nail assembly which is useful in treating fractures occurring in the upper one-third or subtrochanteric portion of the femur. The Zickel nail is a solid intramedullary nail having a single proximal tri-flange cross-nail which is inserted in the direction of the femoral head. The intramedullary rod is curved in two planes to mimic the shape of the femur. The solid cross section does not permit insertion over a guide rod, thus preventing the use of the Zickel nail for comminuted and distal fractures of the femur because the closed surgical technique cannot be practiced. The rigid tri-flange cross-nail is not suitable for use in treating femoral neck fractures because the cross-nail must be locked into position by a set screw to prevent backing out. Adequate compression cannot be achieved. As stated above, the sliding compression screw has been found to be most effective in treating femoral neck fractures.

The commercially available Kuntscher Y-nail includes a flanged cloverleaf shaped intramedullary nail which is inserted through a hole in a single femoral neck nail. The rod includes a longitudinal slit. The Kuntscher device is indicated only for unstable trochanteric fractures. Neither the Kuntscher device, nor the Zickel nail, includes distal anchoring means and both therefore are not useful for treating distal fractures. The femoral neck nail of the Kuntscher device, which is angled toward the femoral neck is locked into place by the intramedullary rod. Thus, the Kuntscher Y-nail is also not indicated for femoral neck fractures.

A bone-nail which permits left-right orientation by means of "criss-cross" nail holes is shown by Enter U.S. Pat. No. 4,475,545.

For unstable subtrochanteric fractures, the extreme loads have frequently caused implants, such as hip compression screw plates, to fail. In cases of severe comminution of the femoral shaft, existing interlocking nails have at times not provided adequate strength.

SUMMARY OF THE INVENTION

Current treatment of femoral neck and shaft fractures is done with two nails, a femoral nail (for shaft fractures) and a recon nail (for combined neck and shaft fractures). The femoral nail has provisions for a single downwardly oblique screw for proximal locking. The recon nail has provisions for twin upwardly oblique locking screws.

The femoral nail can be used bilaterally, while the recon nail is specific for the left or right side. Placement of the upwardly oblique screw is difficult and is not recommended for the treatment of shaft fractures along, and may be risky if used in this manner, therefore recon nails are not used in this manner, therefore recon nails are not used to treat femoral fractures on the same side they are used to fix neck and shaft fractures.

A recon nail can be used as a femoral nail by using it on the opposite limb, e.g. a right recon nail can function as a left femoral nail when inserted in the left leg, one hole is empty and one screw hole accommodates a single downwardly oblique locking screw. However, a single current recon nail can not treat both fractures in one leg. Therefore, a hospital must have available many different femoral and recon nails in different sizes, a large expense.

Occasionally, a femoral neck fracture is found intraoperatively while nailing a simple femoral shaft fracture shaft fracture. In this case, removal of the femoral nail is not recommended as the neck fracture may be compromised. Cannulated screws are placed in the neck around the nail to fix the fracture, a difficult task.

The present invention could be used to treat both femoral neck and shaft fractures. The present invention provides an improved intramedullary nail having three proximal locking screw passageways, two upwardly oblique passageways and a single downwardly oblique passageway. The nail of the present invention would reduce the inventory of recon and femoral nails required to fix commonly occurring fractures.

A pair of intramedullary nails of the present invention could replace a femoral and two recon nails, reducing inventory by thirty three percent. Additionally, the surgeon would be able to intraoperatively change from a femoral to recon mode of the nail without risking a displaced neck fracture reducing operating time. The instrumentation required for the intramedullary nail of the present invention would be less than what is currently required for the femoral and recon nails, making the operating room supply room less cluttered.

The present invention provides an improved intramedullary nail implant for use in the repair of a patient's femur. The apparatus of the present invention can be either a one piece integral nail or a modular nail that includes nail body having connectable upper end, middle and lower end portions and a central longitudinal bore. Taper lock or morse taper connections can be used between the sections to connect them together end to end.

The upper end portion of the nail body carries an enlarged head having a hollow bore that communicates with the central longitudinal bore and with an axis that is coincident with the central longitudinal axis of the nail body.

The proximal section has a cylindrically shaped wall that surrounds the hollow bore and provides a wall thickness that is greater than the wall thickness of the middle and lower end portions of the nail body.

The wall of the proximal section carries five openings therethrough including a first group of three openings and a second group of two openings, the groups being positioned about 180 degrees apart from each other.

The first group of openings includes two generally parallel, lower openings and a third upper openings having a central axis that forms angle with the axis of each of the two lower openings. The second group of openings include two openings one aligned generally with the axis of one of the parallel openings of the first group of openings and another opening that is the largest of all of the openings, comprising two intersecting cylindrical bores.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein:

FIG. 1 is a fragmentary elevational sectional view of the preferred embodiment of the apparatus of the present invention;

FIG. 2 is a fragmentary elevational view of the preferred embodiment of the apparatus of the present invention;

FIG. 3 is another fragmentary elevational sectional view of the preferred embodiment of the apparatus of the present invention;

FIG. 4 is an elevational view of the preferred embodiment of the apparatus of the present invention showing the femoral mode;

FIG. 5 is an elevational view of the preferred embodiment of the apparatus of the present invention illustrating the recon mode;

DETAILED DESCRIPTION OF THE PREFERRED EMBODIMENT

Figure 6:
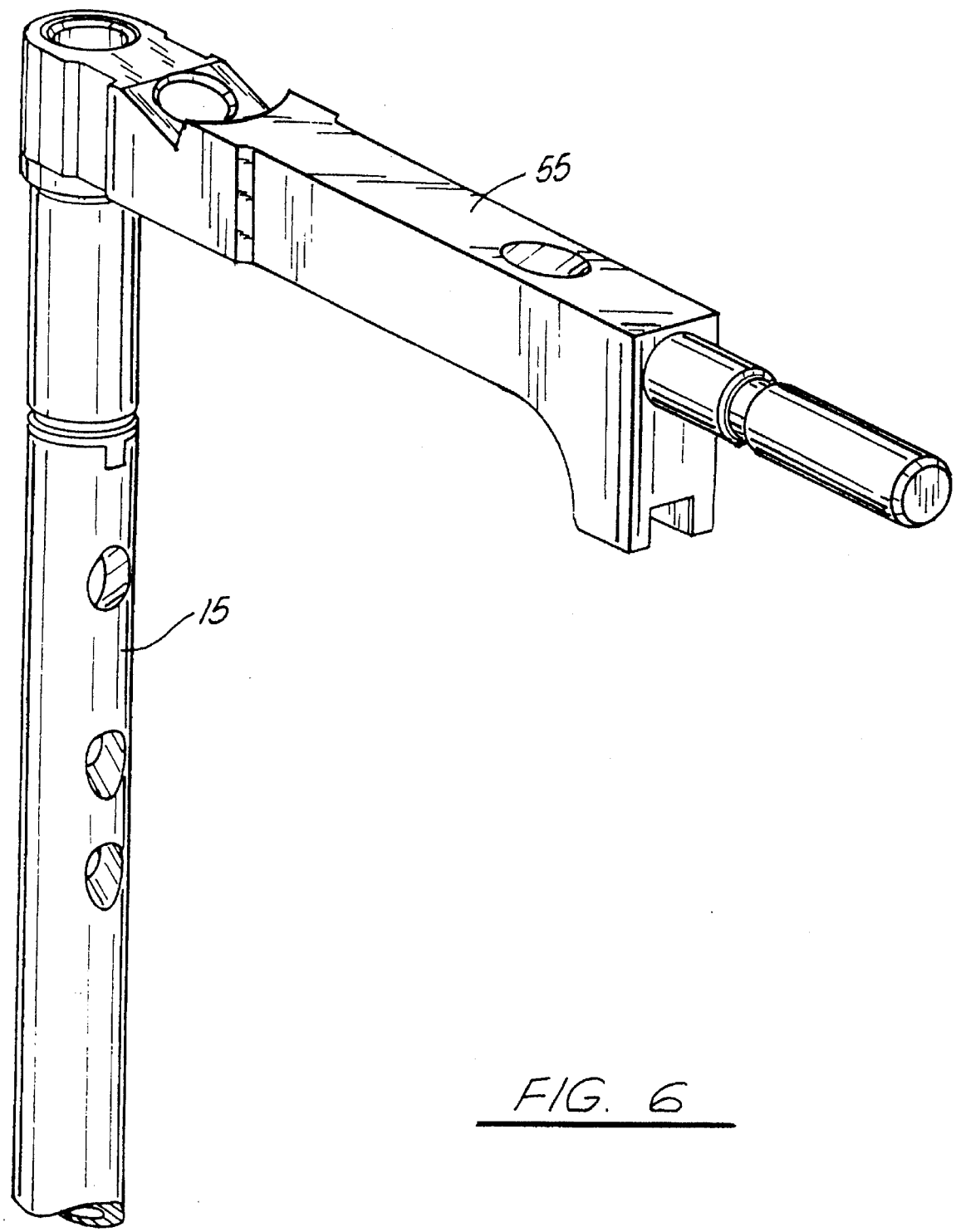
FIG. 6 is a perspective view of the preferred embodiment of the apparatus of the present invention shown in use with a drill guide attached.

FIGS. 1–5 show generally the preferred embodiment of the apparatus of the present invention designated generally by the numeral 10. Intramedullary nail 10 includes a nail body 11 that can be an integral nail body or modular. In FIGS. 1–5, a modular nail is shown, wherein the proximal end 12 is in the form of a head 15 having a tapered socket 16 that connects to middle 14 which then connects to distal 13 section (see FIG. 4). The construction and use of such a modular intramedullary nail in general can be seen in prior U.S. patent application Ser. No. 08/275,806 filed Jul. 14, 1994 naming Brosnahan, James, Lee and Russell as inventors, incorporated herein by reference.

Head 15 includes a socket 16 for forming a connection such as a taper lock connection with an adjoining middle nail section 14. Intramedullary nail 10 provides a central longitudinal bore. Bore 17 (FIG. 2) is a longitudinally extending bore for the nail below head 15. The head 15 provides a central longitudinal bore 18. In the preferred embodiment, the bores 17, 18 have a common central longitudinal axis 20.

Head 15 provides an open top 19. The bore 18 can be threaded at open top 19 for aiding in the removal of nail 10. Further, the open top 19 provides a place for attachment of a drill guide 55 thereto (see FIG. 6).

A plurality of five openings 21–25 extend through the wall 15A of head 15. These five openings 21–25 combine to provide three separate passageways for accepting bone screws 40, 41.

In FIG. 1, the openings 23 and 24 are cylindrically shaped openings that have a common axis 26. The opening 25 is a large opening (see FIG. 3) that is formed of a pair of intersecting cylindrical sections 29, 30 forming opposed projections 31, 32 as shown in FIG. 3. The cylindrical sections 29, 30 each have a central axis 27, 28 respectively. The angle formed by axes 27, 28 is preferably between 70° and 105°, preferably 85°.

The cylindrically shaped sections 29, 30 of enlarged opening 25 cooperate respectively with openings 21, 22. The opening 21 is a cylindrically shaped opening having axis 28 that is a aligned with the cylindrical section 29 of opening 25. Thus, a bone screw can be placed in the passageway along axis 28 through opening 21 and cylindrical section 29 (see FIG. 4). Similarly, a bone screw can be place in the passageway along axis 27 through opening 22 and cylindrical section 30 of opening 25. Each of the axes 26, 27 form an acute angle of between 30° and 65° with the central axis 20 of nail 10, preferably 45°.

In FIGS. 4 and 5, the femoral mode (FIG. 4) and the recon mode (FIG. 5) are illustrated with respect to a patient's femur 51, femoral head 52, femoral neck 53, and intramedullary canal 54.

In FIG. 4, bone screw 39 has been placed through the passageway defined by opening 21 and cylindrically shaped section 29 of opening 25. Bone screw 39 has an unthreaded smooth cylindrically shaped section 42 with an outer surface that conforms to the inside wall 33 of opening 21 and the inside wall 37 of cylindrical section 29.

In FIG. 5, the recon mode is shown with bone screws 40, 41 being positioned respectively through openings 22 and 23. The bone screw 40 extends along axis 27 through the passageway defined by opening 22 and cylindrical section 30 of opening 25. The bone screw 41 extends along axis 26 through the passageway defined by opening 23 and opening 24.

The smooth unthreaded sections 43, 44 of bone screws 40, 41, respectively engage the inside walls 34, 38 and 35, 36. In FIGS. 4 and 5, each of the bone screws 39–41 provide threaded sections 45, 46, 47 respectively. Further, each bone screw 39–41 provides an enlarged head portion 48–50.

The following table lists the parts numbers and parts descriptions as used herein and in the drawings attached hereto.

| PARTS LIST | |
|---|---|
| Part Number | Description |
| 10 | intramedullary nail |
| 11 | nail body |
| 12 | proximal end |
| 13 | distal end |
| 14 | middle |
| 15 | head |
| 15A | wall |
| 16 | tapered socket |
| 17 | bore |
| 18 | bore |
| 19 | open top |
| 20 | central longitudinal axis |
| 21 | opening |
| 22 | opening |
| 23 | opening |
| 24 | opening |
| 25 | opening |
| 26 | axis |
| 27 | axis |
| 28 | axis |
| 29 | cylindrical section |
| 30 | cylindrical section |
| 31 | projection |
| 32 | projection |
| 33 | inside wall |
| 34 | inside wall |
| 35 | inside wall |
| 36 | inside wall |
| 37 | inside wall |
| 38 | inside wall |
| 39 | bone screw |
| 40 | bone screw |
| 41 | bone screw |
| 42 | unthreaded section |
| 43 | unthreaded section |
| 44 | unthreaded section |
| 45 | threaded section |
| 46 | threaded section |
| 47 | threaded section |
| 48 | head |
| 49 | head |
| 50 | head |
| 51 | femur |
| 52 | femoral head |
| 53 | femoral neck |
| 54 | intramedullary canal |
| 55 | drill guide |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. An intramedullary nail implant for use in repair of a patient's femur, comprising:

a) an elongated nail body having a central longitudinal axis and an upper end portion, a lower end portion and a central longitudinal bore the nail body including a proximal nail component and a distal nail component;

b) the proximal nail component defining a head, the head having a hollow bore that communicates with the central longitudinal bore and with an axis that is coincident with the central longitudinal axis of the nail body, the head having a cylindrically-shaped head wall surrounding the hollow bore;

c) the head wall carrying first and second pluralities of openings therethrough that are respectively positioned in the head wall about one hundred eighty degrees apart from each other;

d) the first plurality of openings including first and second generally parallel, lower openings each having an axis and a third upper opening having a central axis that forms an angle with each axis of the first and second lower openings; and e) the second plurality of openings comprising fourth and fifth openings, the fourth opening being closer to the lower end portion than the other and having an axis aligned generally with the axis of the first parallel opening, the fifth opening being a common opening comprised of first and second intersecting cylindrical bores;

f) the first bore having an axis generally aligned with the axis of the second opening, and the second bore having an axis generally aligned with the axis of the third opening;

g) the distal nail component being substantially longer than the proximal nail component; and h) corresponding interlocking connecting members for interconnecting the proximal and distal nail components end-to-end.

2. The implant of claim 1 wherein the axes of the intersecting cylindrical bores form an angle of between 70 and 105 degrees.

3. The implant of claim 1 wherein the axes of the first and second openings form an angle of between 30 and 65 degrees with the central longitudinal axis of the nail body.

4. The implant of claim 1 further comprising at least one bone screw that closely fits two of the openings and intersects the hollow bore.

5. The implant of claim 1 wherein the first and second intersecting cylindrical openings define a pair of projections each projection being the same distance from each of the end portions of the nail body.

6. The implant of claim 1 wherein the proximal and distal nail components define a modular nail body of a plurality of interconnectable sections.

7. An intramedullary nail implant for use in repair of a patient's femur, comprising:

a) an elongated nail body having an upper end portion, a middle portion and a lower end portion and a central longitudinal bore;

b) the upper end portion carrying a head having a hollow bore that communicates with the central longitudinal bore and with an axis that is coincident with a central longitudinal axis of the nail body, the head having a cylindrically shaped wall surrounding the hollow bore with a wall thickness that is greater than a wall thickness of the middle and lower end portions of the nail body;

c) the wall carrying five openings therethrough including a first group of three openings and a second group of two openings, the groups being positioned about one hundred eighty degrees apart from each other;

d) the first group of openings including first and second generally parallel, lower openings and a third upper opening with generally parallel axes having a central axis that forms an angle with the axis of each of the two lower openings; and e) the second group of openings including fourth and fifth openings, the fourth opening aligned generally with the axis of the first parallel openings and the fifth opening that is the largest of all of the openings, and comprising two intersecting cylindrical bores;

f) the first bore having an axis generally aligned with the axis of the second opening, and the second bore having an axis generally aligned with the axis of the third opening.

8. An intramedullary nail implant for use in repair of a patient's femur, comprising:

a) an elongated nail body having an upper end portion, a lower end portion and a central longitudinal bore;

b) an enlarged head at the upper end portion, the head having a hollow bore that communicates with the central longitudinal bore and with an axis that is coincident with a central longitudinal axis of the nail body, the head having a cylindrically shaped wall surrounding the hollow bore;

c) the wall carrying first and second pluralities of openings therethrough that are positioned about one hundred eighty degrees apart from each other;

d) the first plurality of openings including first and second generally parallel, lower openings and a third upper opening with generally parallel axes having a central axis that forms an angle with the axis of each of the two lower openings; and e) the second plurality of openings including fourth and fifth openings, the fourth opening having an axis aligned generally with the axis of the first parallel openings and the fifth opening having first and second intersecting cylindrical bores;

f) the first bore having an axis generally aligned with the axis of the second opening, and the second bore having an axis generally aligned with the axis of the third opening.

* * * * *